(12) United States Patent
Hagenbuch et al.

(10) Patent No.: US 6,641,398 B2
(45) Date of Patent: Nov. 4, 2003

(54) DENTAL MATERIALS CONTAINING A TEAR-OFF MATERIAL

(75) Inventors: Konrad Hagenbuch, Grabs (CH); Gerhard Zanghellini, Schaan (LI)

(73) Assignee: Ivoclar Vivadent AG (LI)

( * ) Notice: Subject to any disclaimer, the term of this patent is extended or adjusted under 35 U.S.C. 154(b) by 0 days.

(21) Appl. No.: 09/933,024

(22) Filed: Aug. 20, 2001

(65) Prior Publication Data

US 2002/0040074 A1 Apr. 4, 2002

Related U.S. Application Data

(60) Provisional application No. 60/263,654, filed on Jan. 23, 2001.

(30) Foreign Application Priority Data

Aug. 21, 2000 (DE) .......................... 100 40 780

(51) Int. Cl.$^7$ ................ C08F 2/46; A61C 5/10
(52) U.S. Cl. ........ 433/223; 433/213; 433/218; 433/221; 433/222.1; 433/226; 433/227; 523/113; 523/115; 523/300; 522/908; 522/150; 522/151; 522/152; 522/153; 522/157; 522/161
(58) Field of Search ................ 433/213, 218, 433/221, 222.1, 223, 226, 227; 264/16, 17, 18, 19, 20; 523/115, 113, 300; 522/908, 150, 151, 152, 153, 157, 161

(56) References Cited

U.S. PATENT DOCUMENTS

| | | | | | |
|---|---|---|---|---|---|
| 3,082,531 A | * | 3/1963 | Jacobson | ...................... | 433/39 |
| 3,421,222 A | * | 1/1969 | Newman | ...................... | 433/36 |
| 4,478,771 A | * | 10/1984 | Schreiber | ...................... | 264/454 |
| 4,563,152 A | * | 1/1986 | McClure | ...................... | 433/39 |
| 4,608,021 A | * | 8/1986 | Barrett | ...................... | 433/229 |
| 5,015,180 A | * | 5/1991 | Randklev | ...................... | 433/9 |
| 5,098,304 A | * | 3/1992 | Scharf | ...................... | 433/215 |
| 5,183,397 A | * | 2/1993 | Weissman | ...................... | 433/215 |
| 5,444,104 A | | 8/1995 | Waknine | | |
| 5,620,322 A | * | 4/1997 | Lococo | ...................... | 433/39 |
| 5,622,496 A | * | 4/1997 | Champagne | ................ | 433/39 |
| 5,839,900 A | | 11/1998 | Billet et al. | | |
| 5,975,906 A | * | 11/1999 | Knutson | ...................... | 433/226 |
| 6,407,148 B1 | * | 6/2002 | Krejci et al. | ................ | 523/116 |

FOREIGN PATENT DOCUMENTS

| | | | |
|---|---|---|---|
| DE | 3632868 A1 | 8/1987 | |
| DE | 4339399 A1 | 5/1995 | |
| WO | WO9925309 | * 5/1999 | ............ A16K/6/00 |

* cited by examiner

Primary Examiner—James J. Seidleck
Assistant Examiner—Sanza L. McClendon
(74) Attorney, Agent, or Firm—Nixon Peabody LLP

(57) ABSTRACT

Dental material containing a polymerizable component and a component applied superficially to the polymerizable component, which can be removed after the curing of the polymerizable material with accompanying formation of a rough surface.

27 Claims, 1 Drawing Sheet

DENTAL MATERIALS CONTAINING A TEAR-OFF MATERIAL

Figure 1:
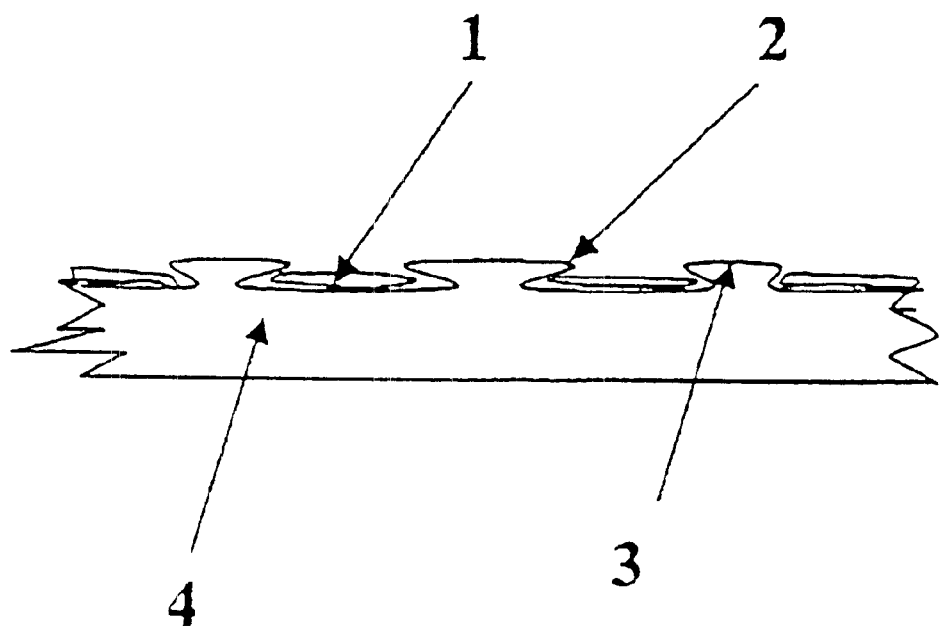

This application claims the benefit of U.S. Provisional Patent Application No. 60/263,654, filed Jan. 23, 2001, which is herein incorporated by reference in its entirety.

The invention relates to dental materials based on polymerizable materials and containing a so-called tear-off material, i.e. a component which, after curing of the polymerizable component, can be removed (torn off) from the cured dental material with accompanying formation of a rough surface.

U.S. Pat. No. 5,839,900 discloses a process for preparing dental restorations in which pieces of fabric impregnated with the organic matrix material are laid onto a cast, shaped by pressing against the cast in a thermoforming process and subsequently cured. After the curing, the basic frame thus obtained is faced by applying a cover material. To ensure a secure adhesion between cover layer and basic frame, the latter is roughened before facing. Damage to the glass fibers embedded in the polymer matrix is often unavoidable, and in addition there is the risk that too much material is removed and unstable structures thus obtained.

DE 31 09 424 A1 discloses a process for manufacturing fiber-reinforced plastics items in which fibers impregnated with curable resins and covered with a flexible, expandable film on one or both sides, are laid onto a suitable mold, matched to this by vacuum-molding and then cured. The films either remain after polymerization on the cured plastic or are removed after curing. In both cases, items with a smooth surface are obtained.

The object of the present invention is the provision of dental materials which, after curing, have a surface which is suitable for direct further processing without additional roughening and cleaning.

This object is achieved by dental materials based on polymerizable substances and containing a component which is applied superficially to the polymerizable component and which can be removed (torn off) after the curing of the Polymerisable component with accompanying formation of a rough surface. The superficially applied component is also called tear-off material hereafter.

Mat-shaped materials which have a structured surface in particular are suitable as superficially applied component or tear-off material. Upon application to the uncured and thus still shapable polymerizable component, the structure of the tear-off material is transferred onto the polymerizable component and the latter is thus embossed with the tear-off material to a certain extent. Upon curing of the polymerizable component, the surface structure is frozen and is retained after the removal of the tear-off material.

Films or preferably fabrics can be used as tear-off material.

By films are meant mat-shaped materials which are characterized by a homogeneous polymer matrix and for example can be prepared by the extrusion of suitable filled or unfilled polymer materials.

Preferably, at least one surface of the films is structured, for example by embossing or perforating. Perforated films are preferred. The perforation allows the passage of polymerizable material which is removed together with the film, on tearing-off of the film, so that a particularly fine roughening of the surface is achieved.

BREIF DESCRIPTION OF DRAWINGS

The function of a perforated film is shown schematically in FIG. 1. FIG. 1 shows a longitudinal section through a polymerizable material 4 covered with a perforated film 1. The section passes through a row of perforations. Some of the polymerizable material has penetrated the perforations 3 and formed disks 2 on the free side of the film. The film is thereby bonded superficially to the polymerizable material upon curing. The disk-shaped extensions 2 of the polymerizable material 4 are removed upon tearing-off of the film together with the film 1.

The perforations preferably have a circular cross-section. A preferred perforated film has perforations with a diameter of approximately 0.4 mm at intervals of approximately 0.5 to 5 mm. The perforations are arranged for example in the form of several rows, the distance between the perforations within the row preferably being 0.5 to 5 mm and the distance between the rows likewise preferably being 0.5 to 5 mm, the individual rows being able to be arranged offset vis-a-vis each other.

By fabrics are meant mat-shaped materials which are woven from threads or fibers. When applying the fabric to the polymerizable component, matrix material can penetrate the fabric and surround the fibers. Upon subsequent curing, the tear-off fabric is bonded to the surface of the material. Upon removal of the tear-off fabric, the matrix film which has penetrated the fabric is torn off the surface of the plastics body, a rough and clean surface being obtained which is suitable for direct further processing.

A further advantage of perforated films and tear-off fabrics is that they allow excess resin to escape. This is removed after the curing together with the fabric.

By using tear-off materials, a time-consuming roughening of the surface, for example by grinding or sand-blasting, is avoided. In the case of fiber composites, the risk of damaging the reinforcing fibers is also averted. As roughening involves a considerable accumulation of dust, the subsequent cleaning of the roughened objects is also simultaneously dispensed with.

Cellulose (also modified types) and thermoplastics, preferably crystalline or semi-crystalline thermoplastics, are particularly suitable materials for the tear-off fabric and tear-off films. Preferred thermoplastic materials are polyolefins, in particular polyethylene (PE), polypropylene (PP) and polyphenylene ether (PPE or PPO), amorphous and/or crystalline polyesters, in particular polyalkylene terephthalate, such as polyethylene terephthalate (PETP or PET) and polybutadiene terephthalate (PBT), polyimides (PI), such as polyetherimide (PEI) and polyamidimide (PA), polyphenylene sulfides (PPS), polyvinyl fibers, polyvinyl chloride (PVC), polyvinylidene chloride (PVDC), copolymers of vinyl chloride and vinylidene chloride or polyvinylidene fluoride (PVDF or PVF2), polyacrylonitrile (PAN), polyarylene sulfide ketones, polyoxymethylene (POM), polycarbonate (PC), polyether (PEth), polyetherketone (PEK), polyether ketone ketones (PEKK), polyether ether ketones (PEEK), polyacetals, polyurethanes (PUR), cellulose esters and copolymers and mixtures of these materials. Particularly preferred are polyalkylene ether terephthalates, in particular polyethylene terephthalate, and polyamides, in particular nylon, preferably nylon 4.6, nylon 8, nylon 6.10, nylon 11 and other nylon types which can be used for textile applications, quite particularly nylon 6, nylon 6.6 and nylon 12.

In addition, glass fibers, regenerate fibers as well as natural fibers such as flax and linen are suitable as fabric materials. By regenerate fibers are meant chemically modified cellulose fibers. Furthermore, high-performance fibers, i.e. fibers with high tensile strength, such as for example aramid fibers (aromatic polyamide fibers) can be used. Suitable aramid fibers are commercially available under the mark Kevlar (DuPont).

If it does not already consist of these materials, the tear-off material preferably has a surface made of polyester, polyethylene or polyamide as these materials can be easily removed from the cured matrix after the polymerization of the polymerizable component.

Due to their good drapability, fabrics with atlas weave (satin weave) and in particular twill weave are preferred. Particularly preferred are fabrics with atlas-1/7 weave and in particular twill-2/2 weave. Such fabrics can be adapted easily to three-dimensional bodies, such as for example, tooth stumps. Other weave types such as e.g. plain weave are particularly suitable for flat surfaces.

The tear-off fabrics preferably have a fabric weight of 20 to 500 g/m$^2$, preferably 40 to 150 g/m$^2$ and particularly preferably approximately 100 g/m$^2$. The fabric weight is adapted to the size of the part to be coated: the smaller the object to be covered, the smaller should be the fabric weight selected. Fabrics with a fabric weight of 40 to 80 g/m$^2$ give a finer surface whereas fabrics with a fabric weight of >80 to 150 g/m$^2$ give a rougher surface. For the preparation of tooth crowns, a fabric weight of 40 to 70 g/m$^2$ is particularly advantageous for example.

A quite particularly preferred tear-off fabric is nylon fabric with a fabric weight of 98 g/m$^2$ and a 2/2 twill weave.

Fabrics with a thread diameter of 4 to 50 $\mu$m, preferably 10 to 30 $\mu$m, in particular 15 to 25 $\mu$m, quite particularly preferably 18 to 20 $\mu$m, are further preferred.

The tear-off material is matched to the polymerizable component used. The inherent strength of the tear-off material (tear resistance) should be greater than the bond strength between tear-off material and polymerizable component. When using very light fabrics to obtain finely-structured surfaces, the use of so-called high-performance fabrics is therefore preferred in order to ensure a sufficient tear resistance. To reduce the tear-off forces, the surface of the tear-off material can be endowed with anti-stick properties, preferably by applying Teflon powder or polyethylene wax.

A curable component which, in addition to a matrix of polymerizable monomers, oligomers, polymers and/or prepolymers, preferably also contains one or more fillers, particularly preferably a fibrous filler, in particular fiber mats and/or uniaxially oriented fiber bundles, is used as polymerizable component. The simultaneous use of particulate and fibrous fillers is also possible.

As polymerizable constituents, the polymerizable components preferably contain tonically and/or radically polmerizable mono- or multifunctional monomers in particular mono-(meth)acrylates such as methyl-, ethyl-, butyl-, benzyl-, furfuryl- or phenyl(meth)acrylate, multifunctional acrylates and methacrylates such as for example bisphenol-(A)-di-(meth)acrylate, decanediol di(meth)acrylate, butanediol di(meth)acrylate, 1,10-decanediol di(meth)acrylate and/ or 1,12-dodecanediol di(meth)acrylate.

Particularly preferred polymerizable constituents are poly-carbonate di(meth)acrylates, in particular the condensation product from a hydroxyalkyl methacrylate, preferably 2-hydroxyethyl methacrylate, and a bis(chloroformate), preferably triethylene glycol bis(chloroformate)). Polycarbonate tri- or tetra-(meth)acrylates, urethane-di-, tri-, tetra-(meth)-acrylates and mixtures thereof. Monomers of this type are described in DE 36 32 868 A1 and U.S. Pat. No. 5,444,104.

Other particularly preferred monomers are bis-GMA (an addition product of methacrylic acid and bisphenol-A-diglycidyl ether), UDMA (an addition product of 2-hydroxyethyl methacrylate and 2,2,4-hexamethylene diisocyanate), di-, tri- (TEGMA) and tetraethylene glycol di(meth)acrylate, trimethylolpropane tri(meth)acrylate and pentaerythritol tetra(meth)acrylate.

To initiate the radical polymerization, the polymerizable component preferably contains thermal and/or photoinitiators.

Preferred initiators for thermal curing are peroxides such as for example dibenzoyl peroxide, dilauryl peroxide, tert.-butylperoctoate and tert.-butylperbenzoate as well as azobisisobutyroethyl ester, benzpinacol and 2,2-dimethylbenzpinacol.

Preferred photoinitiators are benzophenone and benzoin as well as their derivatives, $\alpha$-diketones and their derivatives such as for example 9,10-phenanthrenequinone, diacetyl and 4,4-dichlorobenzil. Particularly preferred photoinitiators are camphor quinone and 2,2-methoxy-2-phenyl acetophenone and in particular combinations of $\alpha$-diketones with amines as reduction agents, such as for example N-cyanoethyl-N-methylaniline, 4-(N,N-dimethylamino)-benzoic acid ester, N,N-dimethylaminoethyl methacrylate, N,N-dimethylsym.-xylidine or triethanolamine. In addition, acylphosphines, such as for example 2,4,6-tri-methylbenzoyldiphenyl- or bis-(2,6-dichlorobenzoyl)-4-N-propylphenylphosphinic oxide, are suitable as photoinitiators.

For the dual curing of radically and cationically polymerizable systems, diaryliodonium- or triarylsulfonium salts, such as for example triphenyl sulfoniumhexafluorophosphate and -hexafluoro-antimonate, are suitable.

Redox initiator combinations, such as for example combinations of benzoyl- or lauryl peroxide with N,N-dimethyl-sym.-xylidine or N,N-dimethyl-p-toluidine, are used as initiators for a polymerization at room temperature. Other suitable initiators and accelerators are vitamin C und barbituric acid.

Organic and inorganic fibrous materials, in particular fiber mats and/or uniaxially oriented fiber bundles are preferred as fillers. Preferred fiber materials are glass fibers and polyethylene fibers (Spectra, Dynema), polyamide, in particular aramid, fibers (Kevlar) and carbon fibers.

Preferred particulate fillers are amorphous spherical materials based on mixed oxides of $SiO_2$, $ZrO_2$ and/or $TiO_2$(DE 40 29 230 A1), microfine fillers such as pyrogenic silica or precipitation silica, spherical $SiO_2$ particles (precipitated particles) with a grain size of 200 to 700 nm as well as macro- (particle size of 5 ìm bis 200 ìm) or mini-fillers (particle size of 0,5 bis 5 ìm), such as quartz, glass ceramic or glass powder with an average particle size of 0,5 ìm to 5 ìm as well as X-ray opaque fillers such as ytterbium trifluoride.

The mixtures can also contain further additives such as colorants (pigments and dyes), stabilizers, aromatic substances, microbiocidal active ingredients, plasticizers and/or UV absorbers.

According to a particularly preferred version, the polymerizable component is fabric mats or fiber bundles impregnated with a polymerizable matrix. Suitable fiber composites, i.e. combinations of organic matrix, fibrous filler and optionally particulate filler are described in the American patent specification U.S. Pat. No. 5,839,900.

Preferred fiber composites for use with shrinkage materials contain 7 to 94 wt.-% fibrous filler and 6 to 93 wt.-% polymerizable matrix. Particularly preferred are materials which contain 28 to 82 wt.-% and in particular 35 to 65 wt.-% fibrous fillers.

Preferred is a polymerizable matrix based on a mixture of bis-GMA, decanediol dimethacrylate (DDDMA), triethylene glycol dimethacrylate (TEGDMA) and urethane dimethacrylate (UDMA). A particularly preferred polymerizable matrix contains 24.5 to 38.6 wt.-% bis-GMA, 0.3 to 0.5 wt.-% decanediol dimethacrylate, 6.2 to 9.7 wt.-% triethylene glycol dimethacrylate and 0.1 wt.-% urethane dimethacrylate. The percentages relate to the fiber composite.

The proportion of non-fibrous fillers preferably lies in the range from 0 to 30 wt.-%, in particular 2 to 15 wt.-% and particularly preferably in the range from 3.5 to 5.5 wt.-%. According to a quite particularly preferred version, the material contains 3.5 to 5.5 wt.-% highly-dispersed silica as additional filler.

Initiators and optionally accelerators are used preferably in a quantity of 0.01 to 3.0 wt-% each, particularly preferably in a quantity of 0.05 to 1.0 wt.-% each relative to the mass of matrix material. The overall quantity of catalysts and stabilizers is preferably 0.3 to 0.5 wt.-% each based on the overall mass of the fiber composite.

The size and dimensions of the materials are matched to their use in the manufacture of dental restorations such as crowns, bridges, inlays and implant structures. The materials are so shaped that they can cover one or more natural or artificial implants or tooth stumps.

The fabric mats are preferably round with a diameter of 10 to 30 mm, preferably 16 to 24 mm, or rectangular with a length of 15 to 150 mm and a width of 10 to 30 mm, preferably 15 to 25 mm.

The polymerizable component preferably comprises 2 to 10 layers, preferably 3 to 8 layers of the impregnated fabric. The fabric is preferably a glass fabric and preferably has a fabric weight of 20 $g/m^2$ to 500 $g/m^2$, particularly preferably 70 $g/m^2$ to 150 $g/m^2$. In the case of the round fabric mats, 7 to 9 layers, and in the case of rectangular mats 2 to 4 layers of a fabric with a fabric weight of 70 to 150 $g/m^2$ are preferred.

The mats are preferably impregnated with a matrix material of the following composition:

| | |
|---|---|
| bis-GMA: | 60 to 80 wt.-% |
| Triethylene glycol dimethacrylate | 10 to 20 wt.-% |
| Highly-dispersed silicon dioxide | 5 to 15 wt.-% |
| Catalysts | 0.3 to 1.5 wt.-% |
| Stabilizers | 0.01 to 0.2 wt.-% |

These materials are particularly suitable for the manufacture of crowns (round shape) or bridges (round and rectangular shape).

Further preferred are impregnated fiber bundles with uni-directional fiber arrangement. These rod-shaped materials preferably have a length of 10 to 160 mm, particularly preferably 10 to 40 mm and a diameter of 2 to 4 mm, preferably 2.5 to 3.5 mm with rectangular or preferably round cross-section. These materials are preferably used in pre-cured form. The rod-shaped materials are for example suitable, together with the round or rectangular materials described above, for the manufacture of bridges.

To manufacture dental restorations, preferably dental material is used which has already been provided with tear-off fabric on one or both sides. A particularly preferred dental material is fiber composite which is coated with tear-off fabric on one or both sides and can be applied directly to a natural tooth stump or a cast and shaped. Rod-shaped materials preferably have the tear-off material wound round them.

Combinations of tear-off material with perforated and/or non-perforated separating films and suction fleeces are possible. Separating films facilitate the removal of dental restorations from molds which are used to shape the materials. Suction fleeces can absorb excess resin which emerges from the polymerizable component upon the shaping or application of the tear-off fabric. Suction fleece or separating film are optionally applied to the tear-off fabric as an additional layer.

A subject of the invention is also a process for the manufacture of dental restorations. In this, the polymerizable material, preferably a fiber composite, is applied to a suitable cast such as for example the reproduction of a natural tooth stump. The polymerizable material is then covered with the tear-off material and shaped, i.e. matched to the cast by for example thermoforming. The polymerizable material is then cured and the tear-off fabric subsequently removed from the surface of the cured material. A rough surface is obtained which is suitable for direct further processing, for example the application of facing materials or crowning.

The manufacture of dental restorations using pieces of fabric which are impregnated with an organic matrix is known per se and is described for example in U.S. Pat. No. 5,839,900. A thermoforming apparatus suitable for carrying out the process is likewise described in U.S. Pat. No. 5,839,900. A preferred apparatus for carrying out the thermoforming process and curing the polymerizable material is marketed by Ivoclar AG, Liechtenstein under the name Vectris VS1 frame work former.

According to a preferred variant of the process, the cast used to prepare the dental restoration is covered with tear-off material and the polymerizable material and a further layer of tear-off material are then applied to the cast. After curing, bodies are obtained which have a tear-off material on both sides. In this way, crowns are for example accessible which are provided with tear-off material on the inside of the crown so that they need not be further roughened by the dentist, which makes the work much easier.

The tear-off fabric can also be applied after the shaping of the polymerizable component. It is essential that the tear-off fabric is applied before the curing of the matrix and that an intensive contact between the polymerizable component and the tear-off fabric is ensured during the application.

To manufacture a crown for example, the tooth to be restored is ground to a stump in a manner known per se. A negative mold is prepared from this stump with impression materials such as for example alginate, polyether or silicon, and this is then cast with a modelling material such as plaster or epoxy resin. In this way, a positive cast is obtained which is insulated e.g. with an alginate solution (in the case of a plaster cast) or a wax solution (in the case of an epoxy cast). The polymerizable component is then applied to the insulated cast stump, as described above, shaped and cured.

After the deep-drawing and polymerization process, excess matrix material is removed for example with a hard metal molding cutter. The crown is then finished with a suitable facing material. To do this, the tear-off fabric is removed from the crown preform and the facing material applied directly to the remaining rough surface. The application is usually carried out in two or more layers, each of the individual layers being cured after the application. After the application of the last layer, the crown is subjected to final curing, polished, cleaned and fitted to the patient by the dentist.

To manufacture a bridge, the two teeth adjacent to the gap in the teeth are ground to stumps by the dentist with suitable instruments in a manner known per se and then a positive cast of the mouth situation is made as described above. Analogously to the manufacture of a crown, each of the stumps is first provided with an unfaced crown. The diastema between the crowned abutment teeth is then filled with polymerizable material. For this, the rod-shaped materials described above are preferably used which can easily be cut to the required length and laid between the abutment teeth. The last layer of the polymerizable material is applied so that it lies at each end on the tooth stumps and preferably covers the whole occlusal surface. Before shaping and curing, the tear-off fabric is removed from the crowns and the polymerizable material, and the latter matched to the cast by deep-drawing and cured. After the curing, a bridge-shaped link is obtained from which excess polymerizable material is removed for example with a hard metal molding cutter.

To manufacture the link, the cast is preferably covered with a silicon impression material, only the link region being left exposed. Preparation of a wax model of the link can be helpful here. The impression material is structured so that an occlusally accessible shape is obtained. The polymerizable material is introduced into the mold from above and shaped and cured as described above.

The cured link is silanized and fitted onto the cast again. The frame of the bridge is then constructed. For this, the link is covered with polymerizable material, preferably in the form of resin-impregnated, rectangular fabric mats, this is shaped by thermoforming and then cured. Excess resin is removed and the cured bridge frame faced after the removal of the tear-off fabric. After polishing and cleaning, the finished bridge can be fitted to the patient by the dentist.

The process according to the invention is characterized by ease of handling and produces dental restorations with a clean, rough surface which can be directly further processed, i.e. for example faced. The fibers of the fiber composite which govern its strength are not destroyed by sand-papering, sand-blasting and similar. By using the tear-off material, a constant, defined surface conditioning is ensured, the roughness of the surface being able to be controlled by using different types of tear-off material. The formation of dust and dirt normally associated with the roughening of surfaces is completely avoided.

A major advantage of the invention is that a weakening or destruction of the uppermost fiber layers of the restoration caused by imprecise wearing away of the cured matrix through grinding or sand-blasting is avoided.

A further embodiment of the invention are kits which contain the materials required for carrying out the process, i.e. at least one polymerizable material and one tear-off fabric. The kits preferably contain several different polymerizable materials, for example round, rectangular and/or rod-shaped material and preferably also suitable facing materials.

What is claimed is:

1. Dental material comprising a polymerizable component and a tear-off component applied superficially to the polymerizable component which can be removed after the curing of the polymerizable component with accompanying formation of a rough surface, wherein the superficially applied tear-off component is a perforated film or a fabric.

2. Dental material according to claim 1, wherein the superficially applied tear-off component is a fabric.

3. Dental material according to claim 1, wherein the superficially applied tear-off component is a perforated film.

4. Dental material according to claim 1, wherein the fabric has a fabric weight of 20 to 500 g/m$^2$.

5. Dental material according to claim 1, wherein the fabric has an atlas weave or twill weave.

6. Dental material according to claim 1, wherein the superficially applied tear-off component contains cellulose, glass or a thermoplastic.

7. Dental material according to claim 6, wherein the superficially applied tear-off component comprises polyethylene, polyamide polyester, or glass.

8. Dental material according to claim 1, wherein the polymerizable component contains filler.

9. Dental material according to claim 8, wherein the filler comprises a fibrous filler.

10. Dental material comprising a polymerizable component and a component applied superficially to the polymerizable component which can be removed after the curing of the polymerizable component with accompanying formation of a rough surface in pre-cured form.

11. Process for manufacturing dental restorations comprising applying a polymerizable material to a cast, applying a perforated film or a fabric tear-off component to the surface of the polymerizable material which can be removed after the curing of the polymerizable material with accompanying formation of a rough surface, curing the polymerizable material, and removing the superficially applied tear-off component from the cured polymerizable material with accompanying development of a rough surface.

12. Kit for manufacturing dental restorations, containing a polymerizable component and a tear-off component according to claim 1.

13. Kit according to claim 12 wherein the polymerizable component contains a fibre composite.

14. Dental material and/or dental restoration product of claim 11.

15. Dental material according to claim 1 in pre-cured form.

16. The method of claim 11, wherein the tear-off component is a perforated film.

17. The method of claim 11, wherein the tear off component is a fabric.

18. Dental material comprising a polymerizable component and an embossed film tear-off component applied superficially to the polymerizable component which can be removed after the curing of the polymerizable component with accompanying formation of a rough surface.

19. Dental material according to claim 18, wherein the superficially applied tear-off component contains cellulose, glass or a thermoplastic.

20. Dental material according to claim 19, wherein the superficially applied tear-off component comprises polyethylene, polyamide polyester, or glass.

21. Dental material according to claim 18, wherein the polymerizable component contains filler.

22. A Dental material according to claim 21, wherein the filler comprises a fibrous filler.

23. Dental material according to claim 18 in pre-cured form.

24. Kit for manufacturing dental restorations, containing a polymerizable component and a tear-off component according to claim 18.

25. Process for manufacturing dental restorations comprising applying a polymerizable material to a cast, applying an embossed tear-off component to the surface of the polymerizable material which can be removed after the curing of the polymerizable material with accompanying formation of a rough surface, curing the polymerizable material, and removing the superficially applied component from the cured polymerizable material with accompanying development of a rough surface.

26. Kit according to claim 24, wherein the polymerizable material contains a fibre composite.

27. Dental material and/or dental restoration product of claim 18.

* * * * *